US008634926B2

(12) United States Patent
Hess et al.

(10) Patent No.: US 8,634,926 B2
(45) Date of Patent: Jan. 21, 2014

(54) CLINIC BASED INSTRUMENT SYSTEM FOR REMOTE PROCESSING AND ACCESS TO IMPLANTED SYSTEMS INFORMATION

(75) Inventors: Michael F. Hess, Minneapolis, MN (US); Christopher M. Manrodt, White Bear Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 923 days.

(21) Appl. No.: 10/936,153

(22) Filed: Sep. 8, 2004

(65) Prior Publication Data

US 2006/0052842 A1    Mar. 9, 2006

(51) Int. Cl.
*A61N 1/372* (2006.01)
(52) U.S. Cl.
USPC .............................................. 607/60; 607/30
(58) Field of Classification Search
USPC .................................. 607/30, 31, 59; 128/903
See application file for complete search history.

(56) References Cited

U.S. PATENT DOCUMENTS

| | | | |
|---|---|---|---|
| 5,576,952 A * | 11/1996 | Stutman et al. ................ | 600/300 |
| 5,752,976 A | 5/1998 | Duffin et al. | |
| 6,169,925 B1 | 1/2001 | Villaseca et al. | |
| 6,240,317 B1 | 5/2001 | Villaseca et al. | |
| 6,249,705 B1 * | 6/2001 | Snell ............................... | 607/59 |
| 6,250,309 B1 | 6/2001 | Krichen et al. | |
| 6,363,282 B1 | 3/2002 | Nichols et al. | |
| 6,418,346 B1 | 7/2002 | Nelson et al. | |
| 6,442,432 B2 * | 8/2002 | Lee ................................. | 607/59 |
| 6,442,433 B1 | 8/2002 | Linberg | |
| 6,480,745 B2 | 11/2002 | Nelson et al. | |
| 6,482,154 B1 | 11/2002 | Haubrich et al. | |
| 6,497,655 B1 | 12/2002 | Linberg et al. | |
| 6,574,511 B2 * | 6/2003 | Lee ................................. | 607/60 |
| 6,599,250 B2 | 7/2003 | Webb et al. | |
| 6,607,485 B2 * | 8/2003 | Bardy ........................... | 600/300 |
| 2001/0027331 A1 * | 10/2001 | Thompson ...................... | 607/60 |
| 2001/0031071 A1 * | 10/2001 | Nichols et al. ................ | 382/115 |
| 2001/0038437 A1 | 11/2001 | Taepke et al. | |
| 2001/0049544 A1 * | 12/2001 | Lee ................................. | 607/59 |
| 2002/0045804 A1 | 4/2002 | Christopherson et al. | |
| 2002/0123672 A1 * | 9/2002 | Christophersom et al. ... | 600/300 |
| 2004/0122487 A1 * | 6/2004 | Hatlestad et al. .............. | 607/60 |
| 2004/0210273 A1 * | 10/2004 | Wang .............................. | 607/59 |

FOREIGN PATENT DOCUMENTS

| | | |
|---|---|---|
| WO | WO0197907 A | 12/2001 |
| WO | WO2006029333 A1 | 3/2006 |

* cited by examiner

*Primary Examiner* — Joseph Dietrich

(57) ABSTRACT

A system for accessing implantable medical device (IMD) data is provided including an interrogation appliance to retrieve data from an IMD and transfer the data to a processor. The processor converts the device data to a viewable form that is transferred by the processor to a data destination. The data destination may be an electronic mail address, a secure web site, a facsimile number or the interrogation appliance. The data is presented in a viewable form at the data destination either on a display or by printing. Any number of interrogation appliances may be communicatively coupled to the processor for converting IMD data and providing the IMD data back to a data destination in a viewable form for use by a clinician.

29 Claims, 5 Drawing Sheets

CLINIC BASED INSTRUMENT SYSTEM FOR REMOTE PROCESSING AND ACCESS TO IMPLANTED SYSTEMS INFORMATION

FIELD OF THE INVENTION

The present invention relates generally to a patient monitoring system and more particularly to a monitoring system including an interrogation appliance for retrieving data from an implantable medical device or devices and transmitting the data to a remote processor for converting and forwarding the data to a desired destination for viewing, storage, or analysis.

BACKGROUND OF THE INVENTION

Implantable medical devices (IMDs) such as cardiac pacemakers, cardioverters and defibrillators (ICDs), hemodynamic monitors, and drug delivery devices, are being offered with increasing capacity for storing physiological and device performance data. Physiological sensors for monitoring various patient conditions such as heart rhythm, blood pressure, respiration, patient activity level, heart wall motion, and blood chemistry may operate in conjunction with an IMD and home based instrumentation for acquiring continuous or periodic physiological data for processing and/or storage by the IMD or for clinical management. Such data may be used by the IMD in automated therapy delivery or by a clinician in diagnosing or monitoring a patient condition and in therapy management.

The development of remote patient monitoring systems allow IMD data to be transferred from the patient's IMD to a home monitor and from the home monitor to a central database so that the data may be reviewed by a clinician without requiring the patient to be present. However, a patient may visit various specialists or other clinicians not associated with the device follow-up clinic. Data stored by the IMD may be useful to such clinicians in combination with information they obtain during an office visit, such as results from physical examination, laboratory tests or patient interview. However, the specialist or other clinician may not have direct access to the central database storing the remote IMD monitoring data. The data in the central database may not be updated at the time the patient is visiting the specialist or other clinician. Therefore it is desirable for a clinician, who may not be affiliated with the IMD follow-up clinic, to be able to gain access to stored IMD data. Clinicians could provide better patient care by having IMD data at hand when evaluating an IMD patient. Since patients having IMDs may be seen at numerous medical care locations, providing a programmer at each facility may not be economically feasible. Furthermore, placement of an IMD programmer in the many facilities that may see IMD patients places training burden on clinicians who may only occasionally see patients having IMDs. What is needed is a system for accessing data from the IMD where the format and content of the provided information can be customized to each facility based on the medical specialty and type of patient assessment to be performed.

BRIEF SUMMARY OF THE INVENTION

The present invention provides a system for accessing IMD data including an interrogation appliance for retrieving data from an IMD and a processor for receiving retrieved data from the interrogation appliance, converting the IMD data to a viewable form, and transferring the converted data to a desired data destination. The desired data destination may be a secure web page, fax machine, e-mail address, or other designated destination associated with a display or printer. The transferred data is then displayed or printed such that it is viewable by a clinician, usually located in the proximity of the patient.

The interrogation appliance includes telemetry circuitry for communicating with the IMD to retrieve all or a subset of stored data. The interrogation appliance is further equipped with a communication unit, which may be a telephone, cable, or wireless modem, for transmitting retrieved data to a processor.

The interrogation appliance may optionally include a display for indicating the status of communication functions. In some embodiments, the interrogation appliance may be the designated data destination and generate a display of converted IMD data received back from the processor. Alternatively, the interrogation appliance may include a printer or electronic storage medium for presenting or storing the IMD data.

The interrogation appliance may include an interface for coupling external monitoring equipment or for enabling a user to interact with the interrogation appliance. Additional data not collected by the IMD may be included in a data transmission to a processor. Such data may be acquired by external monitoring equipment or during physical examination or patient interview. Such externally obtained data may be combined with data retrieved from the IMD by including an interface in the interrogation appliance to allow connection of external devices or user-entered data to be received by the interrogation appliance.

The processor receives raw IMD data from the interrogation appliance via a communications network. The processor performs conversion or translation of IMD data to produce a data file useful and readable by a clinician. The converted IMD data file is forwarded to a data destination via the same or another communication network.

The processor may be included in a remote patient monitoring system associated with a centralized database. A data file forwarded to a data destination by the processor may include data stored in the centralized database to allow trend analysis. Alternatively the processor may be a dedicated processor for converting and transferring data received from an interrogation appliance and may be locally or remotely located relative to the interrogation appliance.

In one aspect of the present invention, the processor is a networked processor for receiving IMD data from any number of interrogation appliances located at various facilities, which may be in different geographic locations.

In another aspect of the present invention, data transferred to a designated data destination may be filtered based on the interrogation appliance identity or the data destination. Filtering may be performed by the interrogation appliance or the processor. The interrogation device may also annotate the IMD data with information regarding the type of assessment performed or some information about when the interrogation occurred to aid in future patient assessment.

In some embodiments, the interrogation appliance may further be used to deliver programming instructions from a centralized processor and database. Programming instructions entered or pending on the centralized database may be transmitted to the interrogation appliance after IMD data has been received and reviewed by the central processor. Programming instructions may then be downlinked to the IMD by the interrogation appliance.

DETAILED DESCRIPTION OF THE PREFERRED EMBODIMENTS

Figure 1A:
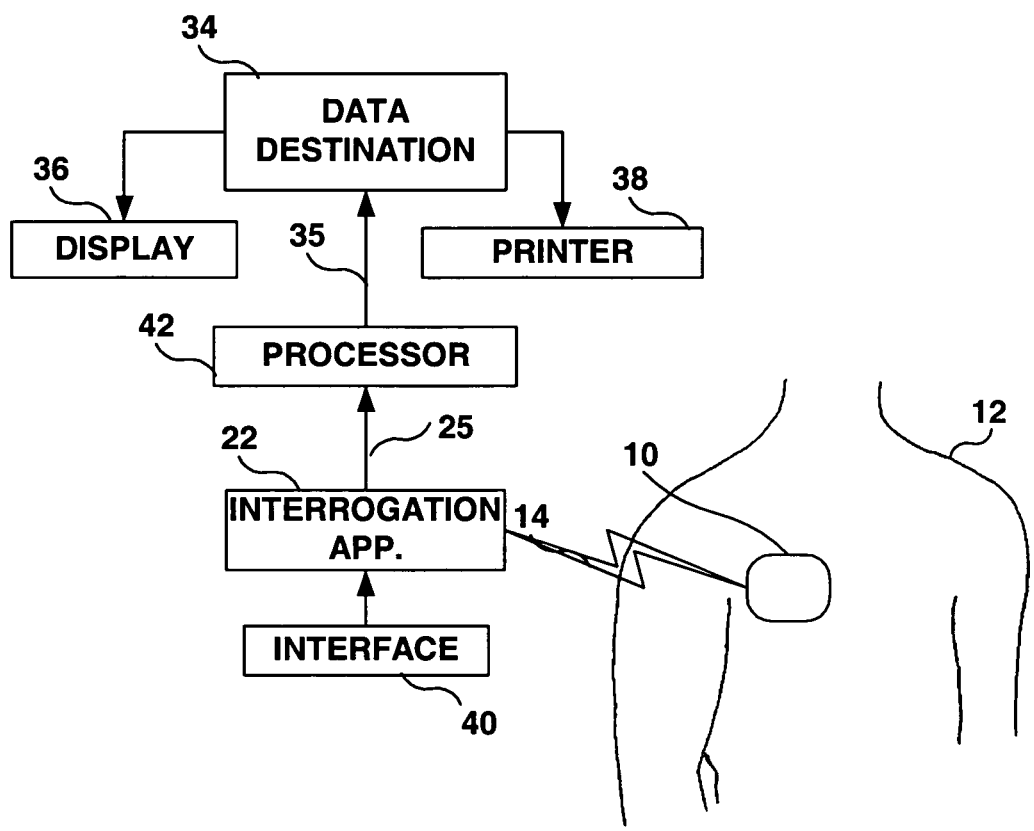
FIG. 1A illustrates a system for accessing IMD data in accordance with the present invention.

FIG. 1A illustrates a system for accessing IMD data in accordance with the present invention. The system shown in FIG. 1A is generally intended for use in a clinic or other third party facility that is not associated with the IMD follow-up clinic or does not otherwise have direct access to an IMD monitoring database or IMD programmer. Device-related and physiological parameters and signals acquired by an IMD and transferred to an IMD monitoring database may be useful to clinician's following the patient but not having an IMD programmer or access to the IMD monitoring database. For example, patients that have an implantable cardiac pacemaker or defibrillator typically see an electrophysiologist for device follow-up. However, these patients may also be seen in a heart failure management clinic, a Coumadin clinic, an emergency room, a dialysis unit, or other medical facility not equipped with a programmer for interrogating the IMD and not having access to a remote IMD monitoring database. Nonetheless, the data stored by the IMD may be valuable to these clinicians in managing the patient disease or doing an assessment of device function. The system shown in FIG. 1A is intended to give a clinician or other third party access to IMD data without providing access to full programmer capabilities which would require a higher level of skill and knowledge regarding the IMD. In particular, the system shown in FIG. 1A is intended to provide low-risk, read-only IMD data accessibility to clinicians or other third parties having an interest in IMD data.

In FIG. 1A, an IMD 10 is shown implanted in a patient 12. When the patient 12 is visiting a clinic or other third party facility, an interrogation appliance 22 located in the clinic or facility can be used by a clinician to establish a communication link 14 with IMD 10 for retrieving data from IMD 10. The interrogation appliance 22 may be configured to retrieve all data stored by IMD 10 or only a subset of IMD data. Retrieved data may also include real-time data acquired by IMD 10. For example, an interrogation appliance may be configured to retrieve only certain IMD data relevant to a particular clinician's interest or specialty. All or a subset of the retrieved data is then be transferred to processor 42. Data retrieved from IMD 10 may remain stored in IMD memory or may be cleared after retrieval by interrogation appliance 22.

Interrogation appliance 22 is adapted to communicate with a processor 42 via communication link 25. Processor 42 converts retrieved IMD data to a usable data form that may be presented in a viewable format for the clinician. As used herein, conversion of data to a "viewable" form refers to any alpha-numeric or graphical data format that is readable by a clinician. Data retrieved from the IMD is initially in a device format that is generally unreadable by a clinician in its raw form.

Processor 42 executes data conversion algorithms as well as other data processing or analysis to produce a readable data set presenting IMD data signals or parameters. "IMD data" as used herein refers to any data acquired for storage or real-time transmission by IMD 10. Such data may include device-related data, such as device performance parameters or diagnostic test results, and/or physiological parameters or signals measured by sensors associated with IMD 10.

Processor 42 may be located locally or remotely relative to interrogation appliance 22. Communication link 25 between processor 42 and interrogation appliance 22 may be established via a wired communication line, such as a telephone or cable modem, or via a wireless communication link which may be RF communication, satellite communication or any available wireless communication technology such as Bluetooth or WiFi.

In an exemplary embodiment, processor 42 is located at a remote location and is communicatively coupled to multiple interrogation appliances located in various clinics, hospitals or other third party facilities. In this way, processor 42 serves as a central data conversion and processing system for any number of interrogation appliances 22. As such, interrogation appliance 22 may be embodied as a simplified communication unit for data transfer from an IMD 10 to processor 42 without requiring costly, high-level processing technology on board. Providing this simplified embodiment of an interrogation appliance to allow read-only access to IMD data is a low-cost solution to fulfilling a need for IMD data access by clinicians located in numerous, unaffiliated facilities, not directly associated with the IMD monitoring database and not fully trained in IMD programming functions. Low-cost interrogation appliances for IMD data transfer may be located at facilities throughout the world having communication with a central processor 42 for performing high-level data conversion and analysis.

Processor 42 transmits converted data results to a designated data destination 34 associated with the particular interrogation appliance 22 from which data was received. At least a portion of IMD data received by processor 42 from interrogation appliance 22 is transferred to the designated data destination 34 via an appropriate communications network 35, which may be a telephone, cable, or wireless communication network. Processor 42 may include associated long-term memory for storing IMD data. All or a subset of IMD data received from interrogation appliance 22 may optionally be stored by processor 42.

A designated data destination 34 may be a secure Internet-based web site, an email address, or a facsimile number. Data destination 34 is associated with a display 36 and/or printer 38 to allow a viewable form of received IMD data to be generated. A clinician may thus view IMD data on a secure web site or in an electronically mailed document on a computer display, or on a printed facsimile. The clinician may choose to print the web page or electronically mailed document to generate a printed record of the data.

Typically, the IMD data received at the data destination has not been analyzed by a medical expert system for providing diagnostic or therapy management results or recommendations based on IMD data. Rather, data received at data destination 34 will typically include converted raw, parameterized or trend data that may be analyzed and reviewed by the receiving clinician according to his/her medical specialty or interests. When IMD data is received by a secure web site or in an electronically mailed document, the data may be imported into locally running applications or custom programs for further processing and analysis or stored in a local database.

Interrogation appliance 22 may further include an interface 40 for coupling other external medical monitoring equipment to interrogation appliance 22. Additionally or alternatively, interface 40 may be embodied as a user interface to allow a clinician to enter data collected through physical examination, patient interview or other external measurements. Data received by interrogation appliance 22 through interface 40 may be combined with data retrieved from IMD 10 for transmission to processor 42.

IMD data retrieved by interrogation appliance 22 may be a subset of data based on the identity of interrogation appliance 22. An interrogation command sent to IMD 10 from interrogation appliance 22 may include identification code indicating the identity of interrogation appliance 22 and the type of data it is authorized to receive. Alternatively, interrogation appliance 22 may receive all IMD data available but may be configured to transfer only selected data to processor 42. As such, interrogation appliance 22 may include a processor for filtering data to be transferred to processor 42. Data selected for transferring to processor 42 may be predetermined or selectable by a clinician using interface 40.

IMD data may be alternatively or additionally filtered by processor 42. Processor 42 may select data to be transferred to data destination 34 based on the identity of interrogation appliance 22 and/or the designated data destination 34. Data received from interrogation appliance 22 may include appliance identity code. Data received from interrogation appliance 22 may further designate the data destination 34. A designated data destination 34 associated with a particular interrogation appliance 22 may alternatively be stored in memory associated with processor 42. Thus, control over IMD data distribution to authorized recipients may be incorporated in the data access system shown in FIG. 1A by preselecting or filtering the data based on the identity of the interrogation appliance 22 and/or the data destination 34.

Figure 1B:
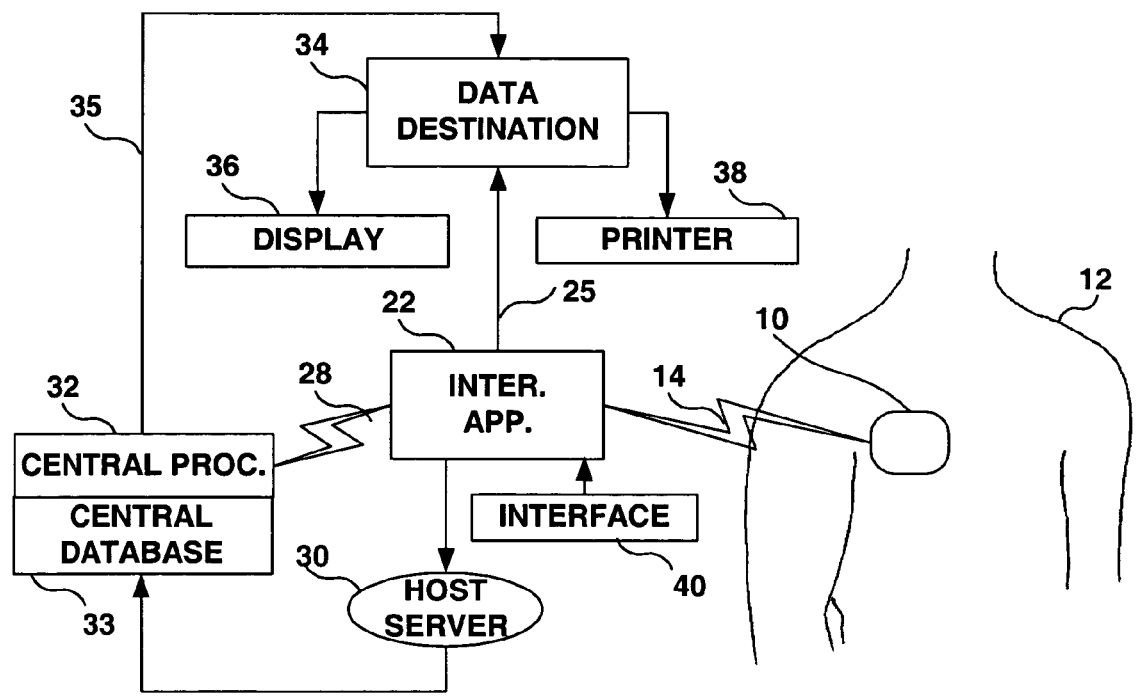
FIG. 1B illustrates a system for accessing IMD data wherein IMD data is processed by a remote IMD monitoring system.

FIG. 1B illustrates a system for accessing IMD data wherein IMD data is processed by a remote IMD monitoring system. Processor 42 shown in FIG. 1A may be dedicated to converting IMD data received from interrogation appliances and transmitting processed data to data destination 34. Alternatively, a processor for converting IMD data received from interrogation appliances may be a processor included in a remote IMD monitoring system. Remote IMD monitoring systems are available wherein a patient using an in-home remote monitor is able to transfer IMD data to a central processor and database for review by a clinician. Examples of such systems are generally described in U.S. Pat. No. 6,599,250 issued to Webb et al., U.S. Pat. No. 6,442,433 issued to Linberg, and U.S. Pat. No. 6,574,511 issued to Lee, U.S. Pat. No. 6,480,745 issued to Nelson et al., U.S. Pat. No. 6,418,346 issued to Nelson et al., and U.S. Pat. No. 6,250,309 issued to Krichen et al., all of which patents are incorporated herein by reference in their entirety.

A remote IMD monitoring system includes a central processor 32 for converting and analyzing IMD data and an associated central database 33 for storing IMD data. Central processor 32 and database 33 may be an Internet-based or other networked system used for remote patient monitoring and may be associated with a medical expert system. Central processor 32 receives data from in-home monitors or programmers for use in remote patient monitoring, for example as described in the above incorporated references.

In accordance with one embodiment of the present invention, central processor 32 also receives IMD data from interrogation appliance 22 via a communication link 28, which may be established via the Internet, a local area network, a wide area network, a telecommunications network or other appropriate communications network, and may be a wireless communication link. Central processor 32 and database 33 may be located at a clinic and receive IMD data from interrogation appliance 22 via a networked host server 30.

Any number of interrogation appliances 22 may be located at various facilities and communicatively coupled with central processor 32 and database 33. Interrogation appliance 22 retrieves IMD data from IMD 10, and transfers the data to central processor 32 via communication link 28. Central processor 32 performs any data conversion and processing necessary to generate an IMD data set that may be presented in a viewable form, either on display 36 or printer 38. Central processor 32 transfers processed IMD data to data destination 34, which may be an email address, a secure web page, or facsimile number as described previously. Central processor 32 may also optionally store received IMD data in central database 33. If such data is stored, an alert message may be generated to notify the clinician(s) responsible for managing the remote monitoring system that new IMD data has been received. Central processor 32 may maintain a log of communication sessions with interrogation appliance 22.

Data processing and transfer operations performed by processor 32 may utilize data previously stored in central database 33. IMD data received from interrogation appliance 22 may be combined with other historical data stored in central database 33 to allow data trend analysis, either by central processor 32 or locally at data destination 34. Data transmitted to data destination 34 may be a subset of retrieved (and stored) data based on the identity of the interrogation appliance 22 sending the IMD data and/or the identity of the data destination 34 receiving the processed data.

Figure 2:
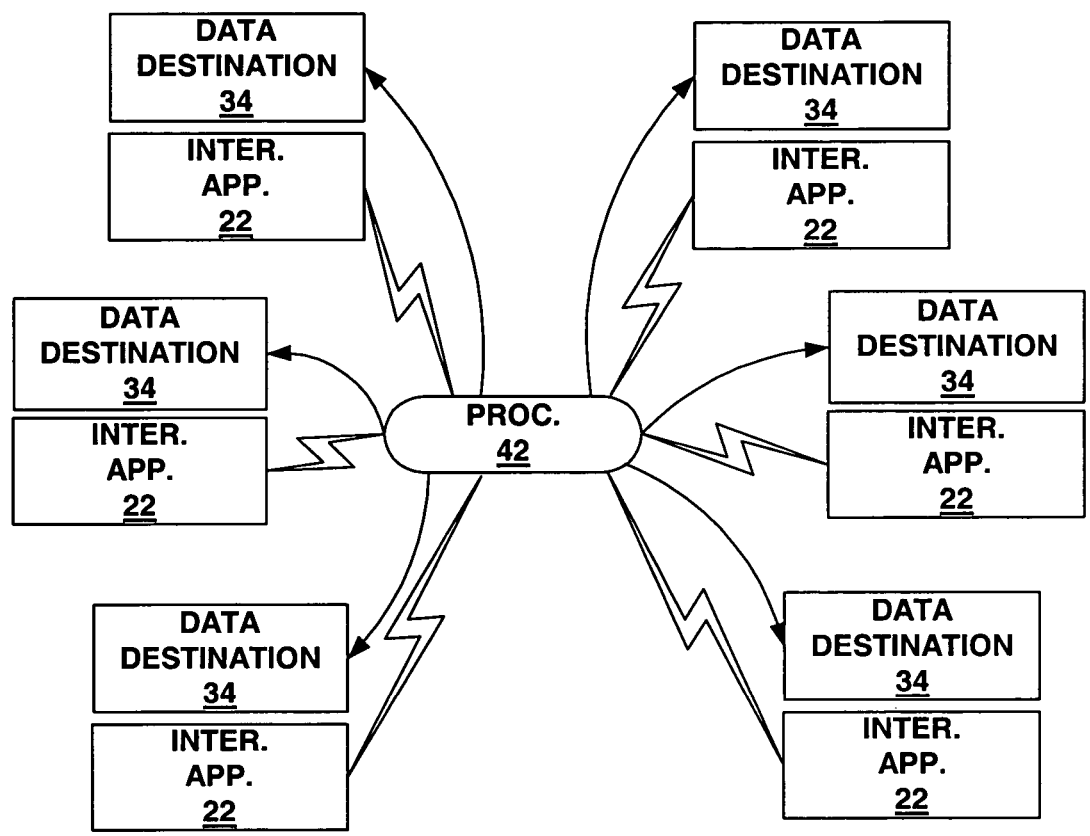
FIG. 2 is a diagram of a networked processor used for converting data received from distributed interrogation appliances.

FIG. 2 is a diagram of a networked processor 42 used for converting data received from distributed interrogation appliances 22. Interrogation appliances 22 may be distributed to numerous facilities at different geographic locations. Interrogation appliances 22 are linked via a communications network to processor 42. When a patient having an IMD visits a facility equipped with an interrogation appliance 22, a clinician may obtain access to IMD data by retrieving IMD data using interrogation appliance 22. IMD data is transferred to high-level processor 42 for data conversion and any other processing or analysis that may be performed by processor 42. Networked processor 42 then transfers the IMD data in a usable form back to a designated data destination 34 associated with the interrogation appliance 22 that has sent the data.

More than one data destination 34 may be associated with an interrogation appliance 22. An interrogation appliance 22 may be used by multiple users at a particular facility for accessing IMD data. Code indicating the designated data destination 34 for receipt of retrieved IMD data may be transferred with retrieved IMD data from interrogation appliance 22 to processor 42. Alternatively, a data destination address or number may be stored by processor 42 in associated memory for use upon receipt of data from a particular interrogation appliance. The interrogation appliance 22 sending IMD data may be identified according to identification code or header information sent with IMD data. Processor 42 uses this information to select the appropriate data destination 34.

Figure 3:
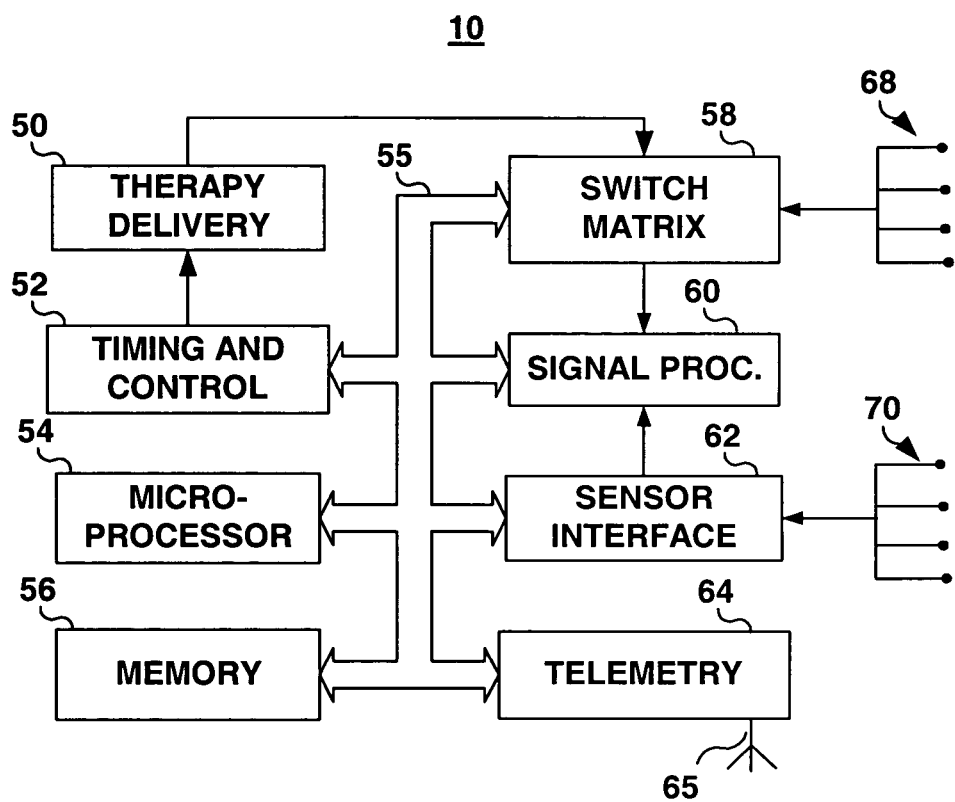
FIG. 3 is a block diagram of typical functional components of an IMD, such as the IMD shown in FIGS. 1A and 1B.

FIG. 3 is a block diagram of typical functional components of an IMD, such as IMD 10 shown in FIG. 1. IMD 10 generally includes timing and control circuitry 52 and an operating system that may employ microprocessor 54 or a digital state machine for timing and controlling sensing and therapy delivery functions in accordance with a programmed operating mode. Microprocessor 54 and associated memory 56 are coupled to the various components of IMD 10 via a data/address bus 55. IMD 10 may include therapy delivery unit 50 for delivering a therapy, such as an electrical stimulation or drug therapy, under the control of timing and control unit 52.

In the case of electrical stimulation therapies, such as cardiac stimulation therapies, therapy delivery unit 50 is typically coupled to two or more electrodes 68 via a switch matrix 58. Switch matrix 58 is used for selecting which electrodes and corresponding polarities are used for delivering electrical stimulation pulses.

Electrodes 68 may also be used for sensing electrical signals within the body, such as cardiac signals, or for measuring impedance. In the case of cardiac stimulation devices, cardiac electrical signals are sensed for determining when an electrical stimulation therapy is needed and in controlling the timing of stimulation pulses.

Electrodes used for sensing and electrodes used for stimulation may be selected via switch matrix 58. When used for sensing, electrodes 68 are coupled to signal processing circuitry 60 via switch matrix 58. Signal processor 60 includes sense amplifiers and may include other signal conditioning circuitry and an analog-to-digital converter. Electrical signals may then be used by microprocessor 54 for detecting physiological events, such as detecting and discriminating cardiac arrhythmias. Electrodes 68 may be used for measuring impedance signals for monitoring, for example, edema, respiration or heart chamber volume.

IMD 10 may additionally or alternatively be coupled to one or more physiological sensors 70. Such sensors may include pressure sensors, accelerometers, flow sensors, blood chemistry sensors, activity sensors or other physiological sensors known for use with IMDs. Sensors 70 are coupled to IMD 10 via a sensor interface 62, which provides sensor signals to signal processing circuitry 60. Sensor signals may be used by microprocessor 54 for detecting physiological events or conditions. For example, IMD 10 may monitor heart wall motion, blood pressure, blood chemistry, respiration, or patient activity. Monitored signals may be stored in memory 78 and may be used for sensing the need for delivering a therapy under control of the operating system. Physiological data may be recorded continuously by IMD 10 or upon a detected triggering event or change in a monitored physiological condition. Acquired physiological data may be stored for later transfer to an external device or transferred in real-time. In accordance with the present invention, acquired physiological data may be transferred to interrogation appliance 22.

The operating system includes associated memory 56 for storing a variety of programmed-in operating mode and parameter values that are used by microprocessor 54. The memory 56 may also be used for storing data compiled from sensed physiological signals and/or relating to device operating history for telemetry out on receipt of a retrieval or interrogation instruction. All of these functions and operations are known in the art, and many are generally employed to store operating commands and data for controlling device operation and for later retrieval to diagnose device function or patient condition. Microprocessor 54 controls device diagnostic functions, such as lead impedance monitoring, stimulation threshold testing, and device longevity estimation. Microprocessor 54 may also manage the storage of device performance parameters such as pacing capture success rate, frequency of delivered therapies, and response to delivered therapies. Device-related parameters acquired by IMD 10 may be transferred to an external monitoring device, such as interrogation device 22 in accordance with the present invention.

IMD 10 is equipped with telemetry circuitry 64 and antenna 65 for bidirectional communication with an external monitor. Programming data and monitoring data are transmitted during downlink or uplink telemetry between IMD telemetry circuitry and external telemetry circuitry included in an external device such as interrogation appliance 22. In an exemplary embodiment, telemetry circuitry 64 and antenna 65 are implemented as a long range telemetry system which allows IMD communication with an external device, such as interrogation appliance 22, to occur without requiring the use of a programming head or wand. Long-range telemetry systems are generally disclosed in U.S. Pat. No. 6,482,154 issued to Haubrich et al., U.S. Pat. No. 6,240,317 issued to Villaseca et al., and U.S. Pat. No. 6,169,925 issued to Villaseca et al., all of which patents are incorporated herein by reference in their entirety. In other embodiments, close range telemetry systems employing a programming head containing a telemetry antenna to be placed over the implanted device may be employed.

Figure 4:
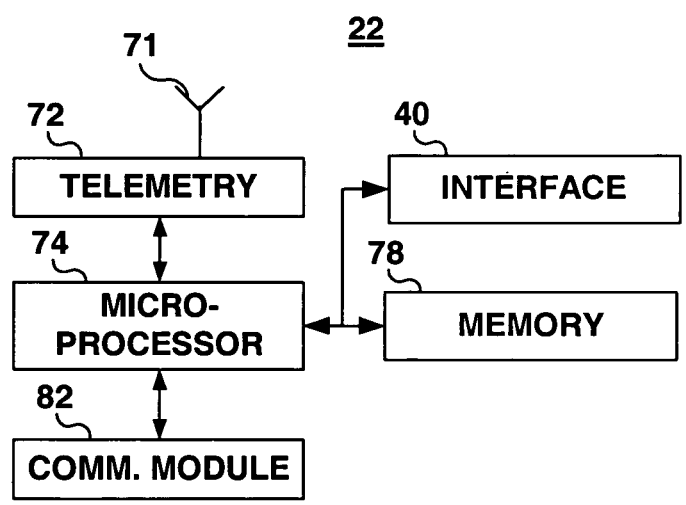
FIG. 4 is a simplified diagram of major functional blocks of the interrogation appliance shown in FIGS. 1A and 1B.

FIG. 4 is a simplified diagram of major functional blocks of the interrogation appliance 22 shown in FIGS. 1A and 1B. Interrogation appliance 22 includes an RF telemetry antenna 71 coupled to a telemetry transceiver and antenna driver circuit board 72 including a telemetry transmitter and telemetry receiver. The telemetry circuitry 72 is coupled to and operated under the control of control circuitry, shown as a microprocessor 74 with associated memory 78. Telemetry circuitry 72 in conjunction with antenna 71 are used to establish bidirectional communication with an IMD for retrieving IMD data. While RF telemetry is typically used to establish communication between an IMD and an external device, other wireless communication technology may be substituted for RF telemetry for enabling bidirectional communication between interrogation appliance 22 and an IMD.

Interrogation appliance 22 is provided with a communication module 82, which may be in the form of a hard-wired or wireless modem, for coupling interrogation appliance 22 with a communications network. IMD data received by interrogation appliance 22 is transferred to a networked processor via communications module 82.

As noted previously, interrogation appliance 22 may optionally be provided with an interface 40 to enable connectivity with external patient monitoring equipment. Interface 40 may additionally or alternatively include a user interface to allow a clinician to enter data obtained during physical examination, patient interview or other external measurements. A clinician may also use interface 40 to select what types of IMD data or parameters are retrieved during a telemetry session. Telemetry sessions between an IMD and interrogation appliance 22 may occur automatically when an IMD is within communication range of interrogation appliance 22. Alternatively, a push-button, touch-screen, or the equivalent may be included in interface 40 to allow a clinician to initiate a telemetry session.

Interrogation appliance 22 includes memory 78 for storing control programs used by microprocessor in controlling the communication functions of the interrogation appliance. Memory 78 may further include data registers for storing data received from an IMD. Data storage capabilities allow received data to be stored until a communication link can be established for transferring data to a central processor. Retrieved data would not be lost in case of an interruption or delay of network communication.

Microprocessor 74 is typically a relatively low-level processor used for controlling communication functions of appliance 22 in transferring data from an IMD to a processor. High-level processing power needed for data conversion is incorporated in a networked processor as described above. However some low-level data processing functions, such as data filtering, may be performed by microprocessor 74. In order to reduce the amount of data or eliminate unwanted data received by a clinician at a designated data destination, IMD data received from an IMD may be filtered by microprocessor 74 prior to transferring the data to a processor. A clinician may be interested in only a portion of or a certain type of data available from an IMD. Interrogation appliance 22 may therefore be configured to filter retrieved IMD data such that excessive amounts of processed data are not received at the designated data destination. Furthermore, with respect to patient privacy, it may be desirable to limit the type of data ultimately being transferred to a data destination for use by a third party. Microprocessor 74 may be pre-programmed to filter data in accordance with a clinician's needs and patient privacy issues. Alternatively, a clinician may use interface 40 to select data to be transferred to a processor.

The interrogation device may also annotate the IMD data with information regarding the type of assessment performed or some information about when the interrogation occurred to aid in future patient assessment. This information may be forwarded with the IMD data to the data destination for record keeping purposes. The information may be additionally stored by the networked processor in a log of communication sessions with interrogation appliances. Interface 40 may be used by a clinician to enter information to be included in the IMD data annotations.

Interrogation appliance 22 may optionally include additional features available in commercially available programmers or in-home monitors. For example appliance 22 may be equipped with a floppy disk drive, CD ROM drive or other electronic data storage medium. Appliance 22 may further include a strip chart recorder or other data recording unit so that a record of received data can be generated. Interrogation appliance 22 may be provided with a display, such as an LED display, for indicating when data transmission is occurring and completed.

In some embodiments, the designated data destination for receiving processed IMD data may be the interrogation appliance 22 itself in which case the interrogation appliance 22 would include display 36 and/or printer 38 (shown in FIG. 1A) for presenting a viewable form of IMD data.

In addition to facilitating retrieval of data from an implanted device, interrogation device 22 may be used in remote programming operations. Operating parameters or programs stored in an IMD for controlling IMD functions may be programmed or updated via interrogation device 22. Programming instructions that may be pending in a central database 33 (FIG. 1B) of a remote monitoring system may be transferred to interrogation appliance 22 via communication module 82 upon receipt and review of IMD data by central processor 32 (FIG. 1B). Examples of remote programming methods which may utilize an interrogation appliance for transferring data to an IMD are generally disclosed in U.S. Pat. No. 6,363,282 issued to Nichols et al., and U.S. Pat. No. 6,497,655 issued to Linberg et al., both of which are incorporated herein by reference in their entirety, and previously incorporated U.S. Pat. No. 6,442,433 issued to Linberg et al.

Thus a system to access IMD data has been described for use by a clinician or other third party, who does not normally have access to or operating knowledge of a full-function IMD programmer or does not have access to data stored in remote monitoring databases. The disclosed system allows for secure distribution of selected IMD data to designated data destinations. The system provides a low cost solution to providing IMD data access by using a networked, high-level processor for converting and processing IMD data received from simplified interrogation appliances that may be placed in numerous facilities at different geographical locations.

Aspects of the present invention have been described herein according to detailed, illustrated embodiments. However it is recognized that numerous variations of these embodiments may be conceived for implementing a system for providing access to IMD data. The various embodiments described herein should therefore be considered exemplary, not limiting, with regard to the following claims.

What is claimed is:

1. A method for accessing implanted medical device data by an interrogation appliance used by multiple users at a medical facility, comprising:
    enabling the interrogation appliance to initiate a telemetry session in response to an implanted medical device being within communication range of the interrogation appliance or in response to a user interface initiation;
    transferring data from an implanted medical device to the interrogation appliance via a wireless communication link, the interrogation appliance comprising an identity code corresponding to an identity of the interrogation appliance itself;
    transferring the interrogation appliance identity code and the data from the interrogation appliance to a processor;
    converting the data to a viewable format;
    filtering the converted data by the processor according to the transferred identity code identifying the interrogation appliance that transferred the data to the processor; and
    transferring the filtered data from the processor to a data destination via a communication network.

2. The method of claim 1 further comprising filtering the data transferred to the data destination according to the data destination.

3. The method of claim 1 further including displaying the converted data received at the data destination.

4. The method of claim 1 further including printing the converted data received at the data destination.

5. The method of claim 1 further including storing the converted data received at the data destination.

6. The method of claim 1 wherein transferring the data from the interrogation appliance to the processor comprises transferring the interrogation appliance identity code for use in filtering the processed data according to the interrogation appliance identity.

7. The method of claim 6, further comprising identifying the data destination in response to the interrogation appliance identity code, the data destination associated with a medical facility at which the interrogation appliance is located.

8. A system for accessing implanted medical device data, comprising:
    an interrogation appliance used by multiple users at a medical facility and adapted for communicating with an implanted medical device for access to IMD data and comprising an identity code corresponding to an identity of the interrogation appliance itself, the interrogation appliance enabled to initiate a telemetry session in response to an implanted medical device being within communication range of the interrogation appliance or in response to a user interface initiation;
    a communication network coupled to the interrogation appliance, the interrogation appliance enabled to initiate a telemetry session for transferring the identity code and the IMD data on the communication network in response to an implanted medical device being within communication range of the interrogation appliance or in response to a user interface initiation;
    a data processor for processing data transferred from the implanted medical device, the data processor coupled to the communication network;

a filter coupled to the data processor for filtering the processed data according to the transferred identity code identifying the interrogation appliance that transferred the data to the processor; and a data presentation unit coupled to the communication network for receiving and presenting data received from the data processor.

9. The system of claim 8, wherein the interrogation appliance comprises:

a telemetry unit for establishing communication with the implantable medical device, a communication module for establishing communication with a processor, a processor for controlling communication functions for retrieving data from the implantable medical device and transferring the retrieved data to the processor.

10. The system of claim 9 wherein the interrogation appliance further comprises an interface.

11. The system of claim 10 wherein the interface is a user interface.

12. The system of claim 10 wherein the interface is configured to receive external monitoring signals.

13. The system of claim 9 wherein the interrogation appliance further includes a display.

14. The system of claim 9 wherein in the interrogation appliance further includes a printer.

15. The system of claim 8 wherein the interrogation appliance comprises a memory storing an appliance identification code indicating the identity of the interrogation appliance for use in filtering the processed data according to the interrogation appliance identity.

16. The system of claim 8, wherein the interrogation appliance is accessible to a plurality of users and the identity code comprises a single identity code for identifying the interrogation appliance.

17. A system for accessing implanted medical device data by an interrogation appliance used by multiple users at a medical facility, comprising:

means for retrieving data from an implantable medical device and comprising an identity code corresponding to an identity of the means for retrieving data itself;

means for transferring the identity code and the retrieved data from the retrieving means to means for processing retrieved data;

means for filtering processed data from processing means according to the transferred identity code identifying the retrieving means that transferred the data to the processing means; and means for transferring filtered data from filtering means to means for presenting processed data in a viewable form.

18. A non-transitory computer-readable medium storing instructions that when implemented in a medical device monitoring system comprising an interrogation appliance used by multiple users at a medical facility cause the system to:

enable the interrogation appliance to establish a first communication link between an implantable medical device and the interrogation appliance in response to an implanted medical device being within communication range of the interrogation appliance or in response to a user interface initiation, the interrogation appliance comprising an identity code corresponding to an identity of the interrogation appliance itself;

transfer data from the implanted medical device to the interrogation appliance;

establish a second communication link between the interrogation appliance and a networked processor;

transfer the identity code and the data from the interrogation appliance to the processor during the second communication session;

convert the transferred data from a device data format to a viewable data format;

filter the converted data according to the transferred identity code identifying the interrogation appliance that transferred the data to the processor;

establish a third communication link between the processor and a data destination; and transfer the filtered data to the data destination.

19. The computer readable medium storing a set of instructions according to claim 18 that further causes the system to present the converted data at the data destination on a display.

20. The computer readable medium storing a set of instructions according to claim 18 that further causes the system to print the converted data on a printer at the data destination.

21. The computer readable medium storing a set of instructions according to claim 18 that further causes the system to electronically store the converted data at the data destination.

22. The computer readable medium storing a set of instructions according to claim 18 that further causes the system to clear data from the implantable medical device after transferring the data from the implantable medical device to the interrogation appliance.

23. The computer readable medium storing a set of instructions according to claim 18 that further causes the system to store the data received by the processor from the interrogation appliance in a database associated with the processor.

24. The computer readable medium storing a set of instructions according to claim 23 that further causes the system to generate a data alert message after storing the data in a database associated with the processor.

25. The computer readable medium storing a set of instructions according to claim 18 that further causes the system to update a log of communication sessions between the processor and the interrogation appliance.

26. The computer readable medium storing a set of instructions according to claim 18 that further causes the system to display an indication of the status of a communication session.

27. The computer readable medium storing a set of instructions according to claim 18 that further causes the system to display an indication of the status of the first communication link between the implantable medical device to the interrogation appliance.

28. The computer readable medium storing a set of instructions according to claim 18 that further causes the system to filter the data transferred from the processor to the data destination based on an identity of the data destination.

29. The computer readable medium storing a set of instructions according to claim 18 that further causes the system to:

transfer a set of programming instructions from the processor to the interrogation appliance; and transfer the set of programming instructions from the interrogation appliance to the implantable medical device.

* * * * *